(12) United States Patent
Pienknagura

(10) Patent No.: US 7,018,403 B1
(45) Date of Patent: Mar. 28, 2006

(54) INCLINED STENT PATTERN FOR VULNERABLE PLAQUE

(75) Inventor: Carla Rosa Pienknagura, Menlo Park, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/940,914

(22) Filed: Sep. 14, 2004

(51) Int. Cl.
*A61F 2/06* (2006.01)

(52) U.S. Cl. .................................. 623/1.15; 623/1.16
(58) Field of Classification Search ....... 623/1.11–1.22
See application file for complete search history.

(56) References Cited

U.S. PATENT DOCUMENTS

| | | | |
|---|---|---|---|
| RE30,912 E | | 4/1982 | Hancock |
| 4,553,545 A | | 11/1985 | Maass et al. |
| 4,886,062 A | | 12/1989 | Wiktor |
| 5,133,732 A | | 7/1992 | Wiktor |
| 5,443,497 A | | 8/1995 | Venbrux |
| 5,554,181 A | * | 9/1996 | Das .......................... 623/1.12 |
| 5,662,713 A | | 9/1997 | Andersen et al. |
| 6,241,760 B1 | | 6/2001 | Jang |
| 6,355,059 B1 | | 3/2002 | Richter et al. |
| 6,585,753 B1 | * | 7/2003 | Eder et al. ................. 623/1.15 |
| 2002/0082682 A1 | * | 6/2002 | Barclay et al. ............ 623/1.22 |
| 2003/0195616 A1 | * | 10/2003 | Pinchasik et al. .......... 623/1.16 |
| 2003/0216802 A1 | * | 11/2003 | Chobotov ................... 623/1.13 |
| 2004/0186556 A1 | * | 9/2004 | Hogendijk et al. ......... 623/1.16 |
| 2004/0193246 A1 | * | 9/2004 | Ferrera ....................... 623/1.15 |
| 2004/0220663 A1 | * | 11/2004 | Rivelli, Jr. ................. 623/1.22 |

FOREIGN PATENT DOCUMENTS

EP 0791341 A1 * 2/1996 ................ 623/1.16

OTHER PUBLICATIONS

U.S. Appl. No. 10/802,435, filed Mar. 16, 2004, Lee et al.
Richardson et al., *Influence of Plaque Configuration and Stress Distribution on Fissuring on Coronary Atherosclerotic Plaques*, Lancet, 2(8669), pp. 941-944 (1989).
Loree et al., *Effects of Fibrous Cup Thickness on Circumferential Stress in Model Atherosclerotic Vessels*, Circulation Research, 71, pp. 850-858 (1992).
Cheng et al., *Distribution of Circumferential Stress in Ruptured and Stable Atherosclerotic Lesions: A Structural Analysis With Histopathological Correlation*, Circulation, 87, pp. 1179-1187 (1992).
Veress et al., *Finite Element Modeling of Atherosclerotic Plaque*, Proceedings of IEEE Computers in Cardiology, pp. 791-794, (1993).
Lee et al., *Circumferential Stress and Matrix Metalloproteinase 1 in Human Coronary Atherosclerosis: Implications for Plaque Rupture*, Atherosclerosis Thrombosis Vascular Biology, 16, pp. 1070-1073 (1996).
Vonesh et al., *Regional Vascular Mechanical Properties by 3-D intravascular Ultrasound Finite-Element Analysis*, American Journal of Physiology, 272, pp. 425-437 (1997).

(Continued)

*Primary Examiner*—Suzette J-J Gherbi
(74) *Attorney, Agent, or Firm*—Fulwider Patton LLP

(57) ABSTRACT

A stent for implantation in a body lumen for protecting from rupture a fibrous cap in order to treat vulnerable plaque. One embodiment of the stent includes inclined planar rings joined by interconnecting links. The planar rings are inclined relative to a plane perpendicular to a longitudinal axis extending the length of the stent. The inclined planar rings provide vessel support yet require lower balloon pressures to deploy and exert lower radial stresses so that when appositioned with vulnerable plaque are less likely to rupture the fibrous cap.

20 Claims, 5 Drawing Sheets

OTHER PUBLICATIONS

Beattie et al., *Mechanical Modeling: Assessing Atherosclerotic Plaque Behavior and Stability in Humans*, International Journal of Cardiovascular Medical Science, 2(2), pp. 69-81 (1999).

C. Feezor et al., *Integration of Animal and Human Coronary Tissue Testing With Finite Element Techniques for Assessing Differences in Arterial Behavior*, BED-vol. 50, 2001 Bioengineering Conference, ASME 2001 (2001).

C. Feezor et al., *Acute Mechanical Response of Human Coronary Fibroatheromas To Stenting*, 2003 Summer Bioengineering Conference, Key Biscayne, Florida, pp. 167-138 (2003).

\* cited by examiner

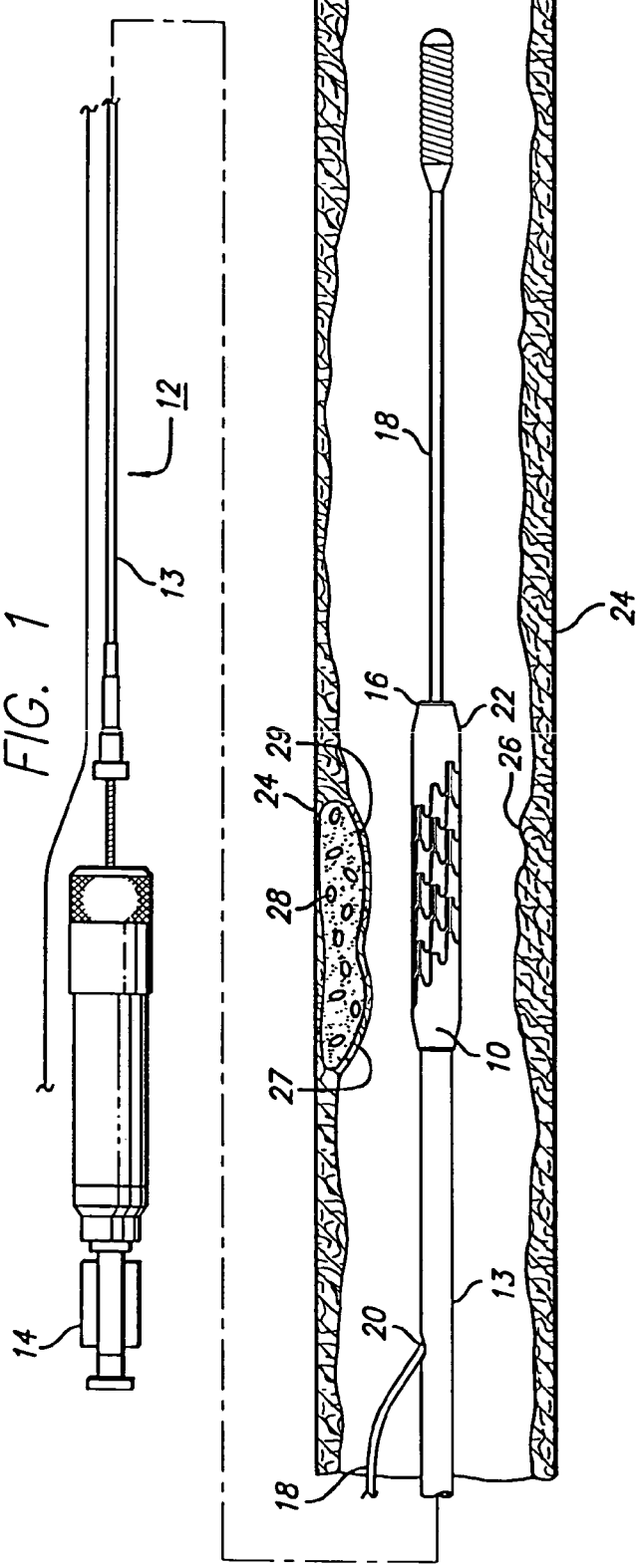
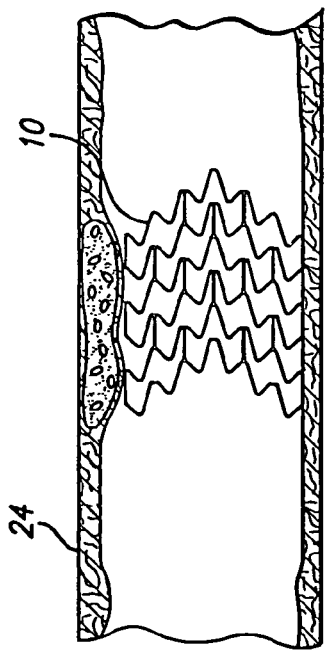
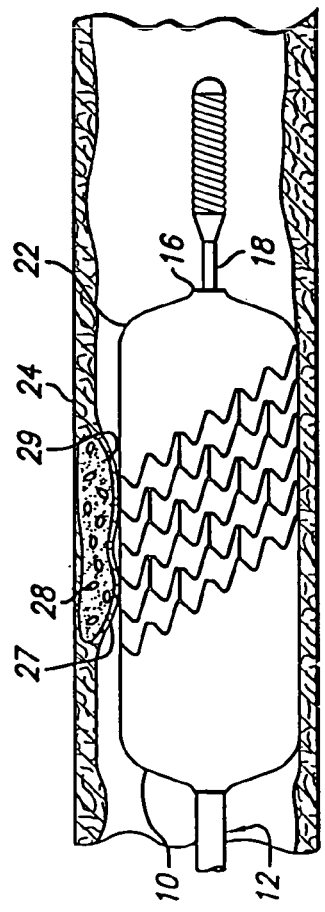

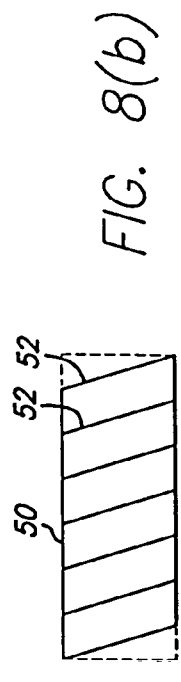
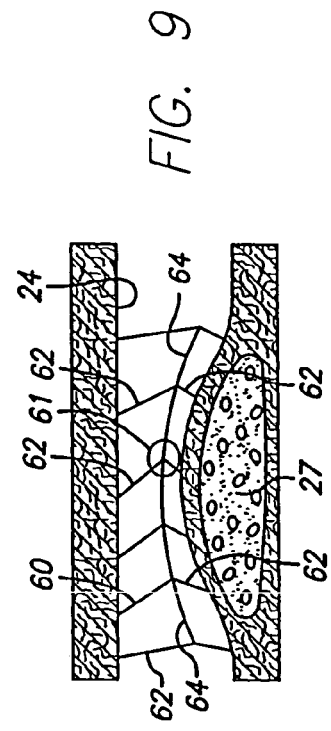
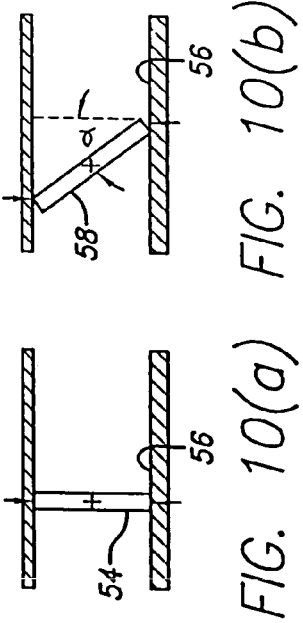
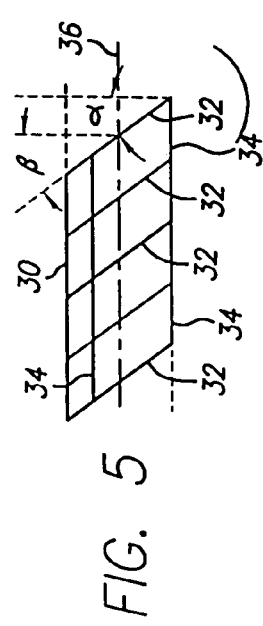
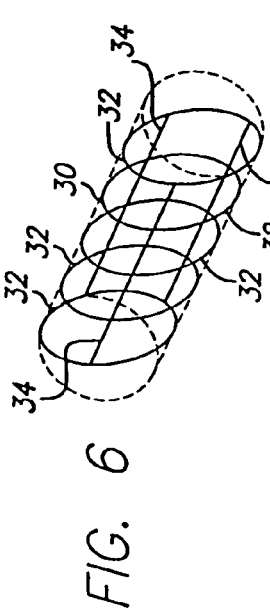
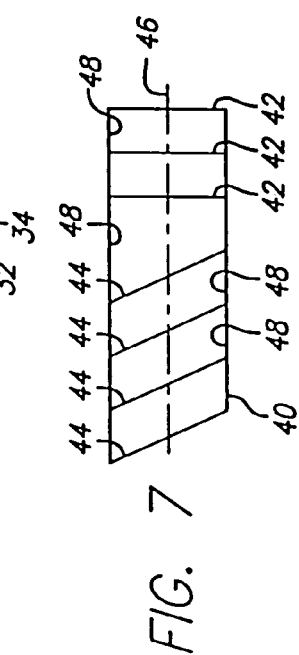

INCLINED STENT PATTERN FOR VULNERABLE PLAQUE

BACKGROUND OF THE INVENTION

The present invention relates to vascular repair devices, and in particular to intravascular stents, which are adapted to be implanted into a patient's body lumen, such as a blood vessel or coronary artery, for the treatment of unstable or vulnerable, human atherosclerotic plaque.

Currently, the treatment of unstable or vulnerable plaque presents a significant therapeutic challenge to medical investigators. Vulnerable plaque is characterized by a basic lesion which is a raised plaque beneath the innermost arterial layer, the intima. Atherosclerotic plaques are primarily composed of varying amounts of long chain extracellular matrix (ECM) proteins that are synthesized by smooth muscle cells. The other primary lesion component of atherosclerotic plaque includes lipoproteins, existing both extracellularly and within foam cells derived primarily from lipid-laden macrophages. In a more advanced lesion, a necrotic core may develop, consisting of lipids, foam cells, cell debris, and cholesterol crystals, and myxomatous configurations with crystalline lipid forms. The necrotic core is rich in tissue factor and quite thrombogenic, but in the stable plaque it is protected from the luminal blood flow by a robust fibrous cap composed primarily of long chain ECM proteins, such as elastin and collagen, which maintain the strength of the fibrous cap. The aforementioned plaque represents the most common form of vulnerable plaque, known as a fibroatheroma. Histology studies from autopsy suggest this form constitutes the majority of vulnerable plaques in humans. A second form of vulnerable plaque represents a smaller fraction of the total, and these are known as erosive plaques. Erosive plaques generally have a smaller content of lipid, a larger fibrous tissue content, and varying concentrations of proteoglycans. Various morphologic features that have been associated with vulnerable plaque, include thinned or eroded fibrous caps or luminal surfaces, lesion eccentricity, proximity of constituents having very different structural moduli, and the consistency and distribution of lipid accumulations. With the rupture of fibroatheroma forms of vulnerable plaque, the luminal blood becomes exposed to tissue factor, a highly thrombogenic core material, which can result in total thrombotic occlusion of the artery. In the erosive form of vulnerable plaque, mechanisms of thrombosis are less understood but may still yield total thrombotic occlusion.

Although rupture of the fibrous cap in a fibroatheroma is a major cause of myocardial infarction (MI) related deaths, there are currently no therapeutic strategies in place to treat these lesions that could lead to acute MI. The ability to detect vulnerable plaques and to treat them successfully with interventional techniques before acute MI occurs has long been an elusive goal. Numerous finite element analysis (FEA) studies have proved that, in the presence of a soft lipid core, the fibrous cap shows regions of high stresses. Representative of these studies include the following research articles, each of which are incorporated in their entirety by reference herein: Richardson et al. (1989), Influence of Plaque Configuration and Stress Distribution on Fissuring of Coronary Atherosclerotic Plaques, Lancet, 2(8669), pp. 941–944; Loree et al. (1992), Effects of Fibrous Cap Thickness on Circumferential Stress in Model Atherosclerotic Vessels, Circulation Research, 71, pp. 850–858; Cheng et al. (1992), Distribution of Circumferential Stress in Ruptured and Stable Atherosclerotic Lesions: A Structural Analysis With Histopathological Correlation, Circulation, 87, pp. 1179–1187; Veress et al. (1993), Finite Element Modeling of Atherosclerotic Plaque, Proceedings of IEEE Computers in Cardiology, pp. 791–794; Lee et al. (1996), Circumferential Stress and Matrix Metalloproteinase 1 in Human Coronary Atherosclerosis: Implications for Plaque Rupture, Atherosclerosis Thrombosis Vascular Biology, 16, pp. 1070–1073; Vonesh et al. (1997), Regional Vascular Mechanical Properties by 3-D Intravascular Ultrasound Finite-Element Analysis, American Journal of Physiology, 272, pp. 425–437; Beattie et al. (1999), Mechanical Modeling: Assessing Atherosclerotic Plaque Behavior and Stability in Humans, International Journal of Cardiovascular Medical Science, 2(2), pp. 69–81; C. Feezor et al. (2001), Integration of Animal and Human Coronary Tissue Testing with Finite Element Techniques for Assessing Differences in Arterial Behavior, BED-Vol. 50, 2001 Bioengineering Conference, ASME 2001; and C. Feezor et al. (2003), Acute Mechanical Response Of Human Coronary Fibroatheromas To Stenting, 2003 Summer Bioengineering Conference, Key Biscayne, Fla., pp. 167–168. Further, these studies have indicated that such high stress regions correlate with the observed prevalence of locations of cap fracture. Moreover, it has been shown that subintimal structural features such as the thickness of the fibrous cap and the extent of the lipid core, rather than stenosis severity are critical in determining the vulnerability of the plaque. The rupture of a highly stressed fibrous cap can be prevented by using novel, interventional, therapeutic techniques such as specially designed stents that redistribute and lower the stresses in the fibrous cap.

Stents are generally tubular-shaped devices which function to hold open a segment of a blood vessel, coronary artery, or other body lumen. They are also suitable for use to support and hold back a dissected arterial lining which can occlude the fluid passageway therethrough.

Currently, there are no known effective methods for treating vulnerable plaque. Conventional stents and stent delivery systems have been used to treat vulnerable plaque. Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

One problem with conventional stents and stent delivery systems is that the conventional stent is typically inflated at a high pressure (e.g., above about 8 atm or 117 psi or higher) in order to reach a nominal dimension (e.g., 3.0–3.5 mm diameter). The required high pressure in turn may cause rupture of the vulnerable plaque and may lead to an acute MI. In addition, conventional stents and stent delivery systems are often designed to keep open a blood vessel's lumen or to provide a rigid support for the vessel. Thus, the stent imparts a certain amount of pressure or force upon the vessel to perform these functions. Using a conventional stent that is designed mainly to keep open the lumen imparts too much radial force and pressure upon the vulnerable plaque causing the vulnerable plaque or the fibrous cap of the vulnerable plaque to rupture.

What has been needed and heretofore unavailable is a stent that can be used to treat a vulnerable plaque by reducing the outward radial stresses exerted by the stent. The present invention satisfies this need and others.

Invention Summary

The present invention is directed to an intraluminal stent that can be used to treat a lesion with vulnerable plaque by reducing the outward radial stresses exerted by the stent. Furthermore, the intraluminal stent can be deployed at a substantially low pressure to minimize trauma to the vulnerable plaque.

In one exemplary embodiment, an intraluminal stent comprises a plurality of planar rings aligned along a common longitudinal axis, wherein each ring is defined by a circumference entirely contained within a plane. The circumferential planes containing the plurality of rings are preferably inclined relative to a plane perpendicular to the longitudinal axis. There is further a plurality interconnecting members having a length extending parallel to the common longitudinal axis and joining adjacent rings.

In various alternative embodiments, the intraluminal stent comprises a first end section, and middle section, and a second end section wherein only the first end section includes at least one ring having the inclined circumferential plane, or wherein only the first and the second end sections include at least one ring having the inclined circumferential plane. Alternatively, the intraluminal stent may have only the first end section and the middle section including at least one ring having the inclined circumferential plane, or wherein only the middle section includes at least one ring having the inclined circumferential plane.

In still further alternative embodiments, the intraluminal stent may have the inclined circumferential planes inclined at an angle $\alpha$ defined by about $30° \leq \alpha \leq 45°$ including all angles between those ranges relative to a plane perpendicular to the longitudinal axis of the stent. The inclined orientation of the rings gives the stent sufficient radial strength for scaffolding yet the stent exerts gentle pressure on the vulnerable plaque. Also, the intraluminal stent may have interconnecting members wherein they form two columns disposed about 180° circumferentially apart or three columns at 120° apart. The use of planar inclined rings and interconnecting members minimize bunching of the rings when deployed or uncontrolled tilt or attitude in the depolyed rings as sometimes seen in coiled spring stents.

The intraluminal stent includes rings that are preferably formed from a serpentine strut pattern having alternating vertices and arms, wherein at least some of the vertices at a peak include a reduced cross-section, a reduced mass section, a void, and/or a groove for reduced strength. Further, the intraluminal stent may include rings having a serpentine strut pattern having alternating vertices and arms wherein at least some of the vertices at a peak of the vertex is radially thinner than the remainder of the vertices for reduced strength, or is narrower in a circumferential width than the remainder of the vertices for reduced strength. Also, the arms but not the vertices may have increased mass, girth, thickness, width, or any combination thereof for improved radiopacity.

The rings of the present invention stent in one embodiment are plastically deformed when balloon expanded if the stent is made from a rather inelastic metal. Typically, the balloon expandable stent is made from a stainless steel alloy or similar material.

The stent may be formed by laser cutting the pattern of rings and links from a tube. The stent also may be formed by laser cutting a flat metal sheet into a pattern of the rings and links, and then rolling the pattern into the shape of the tubular stent. The longitudinal seam where the edges of the sheet meet is then welded or otherwise joined.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a side elevational view, partially in section, of a stent embodying features of the invention and which is mounted on a rapid-exchange delivery catheter and positioned within an artery.

FIG. 2 is a side elevational view, partially in section, similar to that shown in FIG. 1 wherein the stent is balloon expanded within the artery so that the stent embeds within the arterial wall.

FIG. 3 is a side elevational view, partially in section, showing the expanded stent implanted within the artery after withdrawal of the rapid-exchange delivery catheter.

FIG. 4 is a schematic side elevational view of a prior art stent showing conventional upright rings.

FIG. 5 is a schematic side elevational view of the inclined rings of one embodiment of the present invention.

FIG. 6 is a perspective view in schematic form of an inclined ring stent.

FIG. 7 is a schematic side elevational view of another embodiment of the present invention inclined ring stent with a combination of inclined and upright rings.

FIG. 8(a) is a schematic side elevational view showing an inclined ring stent in a crimped or compressed state.

FIG. 8(b) is a schematic side elevational view showing the inclined ring stent of FIG. 8(a) in an expanded or deployed state.

FIG. 9 is a schematic side elevational view showing deployment of the inclined ring stent apposed to the vulnerable plaque.

FIGS. 10(a) and 10(b) show one ring of a prior art stent and one ring of an inclined ring stent, respectively, in the expanded state in the body lumen.

DETAILED DESCRIPTION OF THE PREFERRED EMBODIMENTS

Figure 11:
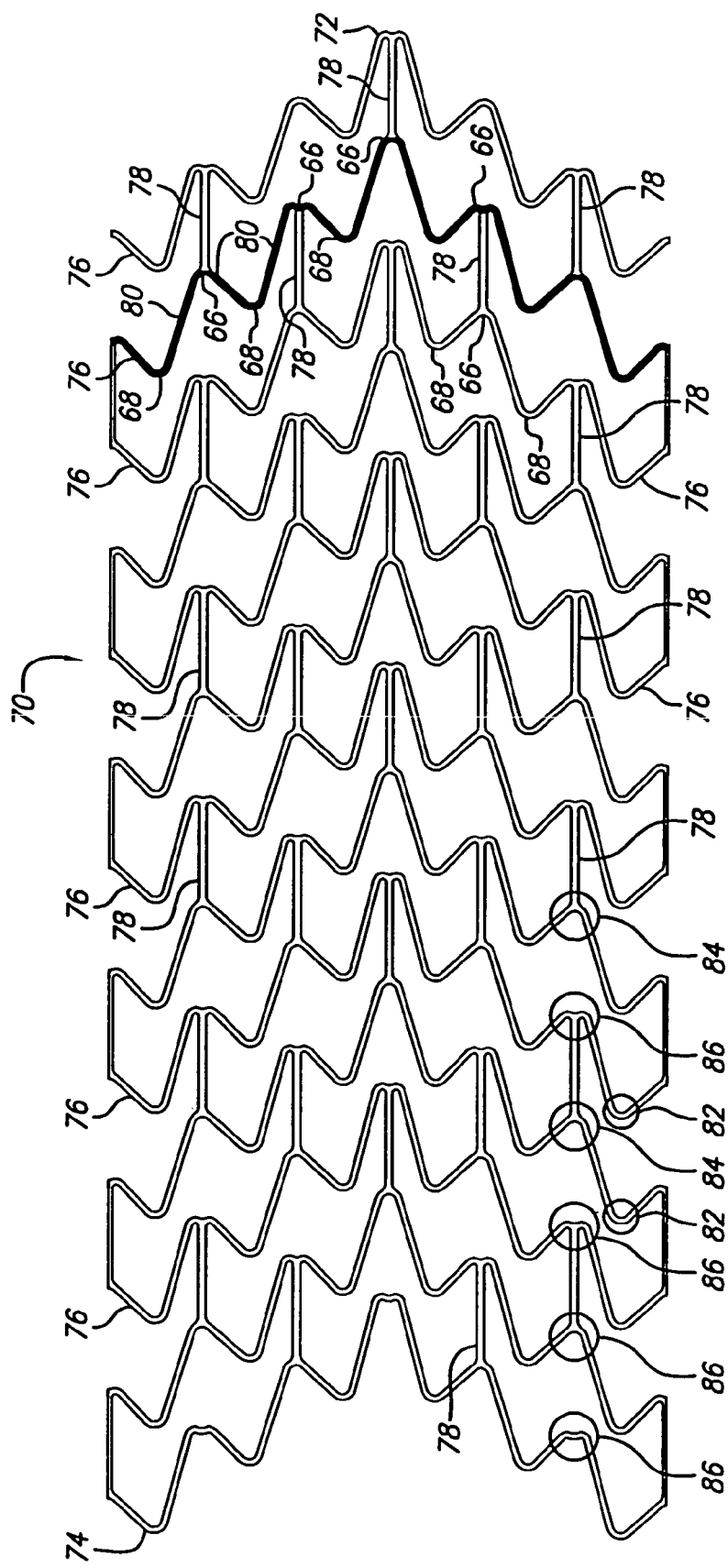
FIG. 11 is one embodiment of the present invention stent unrolled and flattened to show the inclined ring strut pattern.

The present invention is directed to an intravascular stent that can be used to treat a lesion with vulnerable plaque by minimizing the stresses during stent expansion. The present invention stent in one embodiment provides staged balloon expansion through stronger and weaker regions in the cylindrical wall of the stent, and includes anchors positioned at the circumferential transition between the stronger and weaker regions. During implantation, the anchors radially orient and span the weaker region over the vulnerable plaque during the staged expansion. This minimizes cap stresses and reduces the chance of cap rupture.

Turning to the drawings, FIG. 1 depicts one embodiment of the present invention stent 10 mounted on a catheter assembly 12 which is used to deliver the stent and implant it in a body lumen, such as a coronary artery, peripheral artery, or other vessel or lumen within a patient's body. The catheter assembly 12 includes a catheter shaft 13 which has a proximal end 14 and a distal end 16. The catheter assembly 12 is designed to advance through a patient's vascular system by tracking over a guide wire by any of the well-known methods for an over the wire system (not shown) or a well-known rapid exchange catheter system, such as the one shown in FIG. 1.

The catheter assembly 12, as depicted in FIG. 1, is of the rapid exchange (RX) type, which includes an RX port 20 where the guide wire 18 exits the catheter at the distal end 16. This way, the catheter 12 advances along the guide wire 18 on a section of the catheter between the RX port 20 and the catheter distal end 16. As is known in the art, the guide wire lumen which receives the guide wire 18 is sized for receiving various diameter guide wires to suit a particular application. The stent 10 is mounted on the balloon or expandable member 22 and is crimped tightly thereon so that the stent 10 and expandable member 22 present a low profile diameter for delivery through narrow or tortuous arteries.

FIG. 1 further illustrates a partial cross-section of an artery 24, which is shown with a small amount of plaque, a lesion, or a diseased area 26 that has been previously treated by an angioplasty or other repair procedure. The stent 10 is used to repair this diseased or damaged area 26.

The stent 10 may also be used to treat an area with vulnerable plaque 27 which is commonly found in the coronary arteries, peripheral arteries, and other vessels. Vulnerable plaque 27 consists of a thrombogenic lipid 28 that is covered by a thin fibrous cap 29. The stent 10 is configured to deploy under low pressure so as to protect the vulnerable plaque 27 from the expansion forces of the stent 10, thereby reducing the likelihood of inadvertently rupturing the fibrous cap 29 and causing the lipid pool 28 to drain.

In a typical procedure to implant the stent 10, the guide wire 18 is advanced through the patient's vascular system so that the distal end of the guide wire 18 is advanced past the vulnerable plaque 27 or diseased area 26. Prior to implanting the stent 10, a cardiologist may wish to perform an angioplasty procedure or other procedure (i.e., atherectomy) in order to open the vessel and reshape the diseased area 26. Thereafter, the stent delivery catheter assembly 12 is advanced over the guide wire 18 so that the stent 10 is positioned in the target area. Generally, the expandable member or balloon 22 is inflated so that it expands radially thereby expanding the stent 10 radially until the stent is apposed to the vessel wall. The expandable member 22 is then deflated and the catheter 12 withdrawn from the patient's vascular system. The guide wire 18 is typically left in the lumen for post-dilatation procedures, if any, and is subsequently withdrawn from the patient's vascular system.

As depicted in FIG. 2, the balloon 22 is fully inflated with the stent 10 expanded and engaging the vessel wall. In FIG. 3, the implanted stent 10 remains in the vessel after the balloon 22 has been deflated and the catheter assembly 12 and guide wire 18 have been withdrawn from the patient. As further illustrated in FIGS. 2 and 3, the vulnerable plaque 27 is left intact without rupture of the lipid pool 28.

Further details regarding the delivery system may be found in, for example, U.S. application Ser. No. 10/802,435, filed on Mar. 16, 2004, by J. Lee and C. R. Pienknagura, titled "A Stent Deployable At Low Pressue And A Stent Delivery System," whose entire contents are hereby incorporated by reference.

The stent 10 serves to hold open the artery after the catheter 12 is withdrawn, as illustrated by FIG. 3. Due to the construction of the stent 10 from a generally elongated tube, the undulating struts of the stent 10 are relatively flat in a transverse cross-section, so that when the stent 10 is expanded, it is pressed into the wall of the artery and as a result does not interfere with the blood flow through the artery. The stent 10 pressed into the wall of the artery will eventually be covered with smooth muscle cell growth which further minimizes blood flow interference. The undulating struts of the stent also provide good tacking characteristics to prevent stent movement within the artery.

The present invention stent is preferably fashioned from a tube. Conceptually, the tubular form is made from a plurality of rings aligned coaxially along a common longitudinal axis. The rings are joined by interconnecting links.

FIG. 4 depicts in a schematic diagram, in a side elevational view, a prior art stent. The stent has a tubular form with a coaxial arrangement of a plurality of rings, represented as upright vertical lines. The rings are interconnected and are represented by the two continuous horizontal lines.

FIG. 5 is a schematic representing one embodiment of the present invention inclined ring stent 30. To convey the principles of the present invention, a convention is used to describe the inclined rings: the circumference of each ring is generally contained within or defined by a plane. In FIG. 5, the inclined planar rings 32 are depicted as sloped lines, and the interconnecting links 34 are depicted as horizontal lines. In reality, stent 30 has a plurality of inclined rings 32 arranged generally coaxially into a tubular form wherein the inclined rings 32 are interconnected by interconnecting links 34. The inclined rings 32 are also arranged coaxially along a common longitudinal axis 36.

The amount of incline to the ring 32 or to the circumferential plane containing the ring is defined by angle $\alpha$ or based on angle $\beta$, as shown in FIG. 5. Hence, these inclined, planar rings 32 of one embodiment of the present invention stent 30 are clearly oriented differently than the vertical, upright rings in the prior art stent shown in FIG. 4. To be sure, whereas the rings are perpendicularly arranged relative to the longitudinal axis in the prior stent of FIG. 4, the embodiment shown in FIG. 5 has a ring inclination angle $\beta$, for example, as measured between the ring versus a right angle relative to the longitudinal axis 36, where $\beta \neq 90$ degrees. In a preferred embodiment stent, its rings or the circumferential planes containing those rings are inclined at an angle $\alpha$ or $\beta$, defined by about $30° \leq (\alpha$ or $\beta) \leq 45°$ including all angles in between those ranges, when deployed in a body lumen. Most preferably, the inclination angle $\alpha$ or $\beta$=about 30° when the stent is deployed in a body lumen.

The foregoing range of inclination angles gives sufficient hoop strength to the stent for vessel support yet is compliant enough to minimize potential injury to the vulnerable plaque or fibrous cap. Also, the inclined rings require less balloon pressure to deploy, which is another salutary feature for supporting vulnerable plaque.

FIG. 6 is a perspective view again as a schematic of the stent 30 shown in FIG. 5. The stent 30 has a plurality of inclined planar rings or associated circumferential planes 32 arranged coaxially to form a tubular arrangement (indicated in dashed lines) wherein the inclined planar rings or circumferential planes 32 are tilted relative to a vertical plane that is perpendicular to the common longitudinal axis. The inclined rings 32 are joined by interconnecting links 34. In this particular embodiment, the interconnecting links 34 happen to be aligned longitudinally along the length of the stent and are arranged in three columns spaced about 120° circumferentially apart. Of course, other configurations for the interconnecting links 34 are contemplated.

In FIG. 6, it is possible to describe the appearance of the inclined rings as ovals contained within a cylinder or tube. Indeed, looking along the longitudinal axis of the cylinder or tube, the rings appear as ovals, but looking down a line passing through the focus of each planar ring and perpendicular thereto would give the ring the appearance of a circle.

FIG. 7 is a side elevational view of an alternative embodiment stent 40, again depicted in a simplified schematic illustration. The stent 40 contains a combination of upright rings 42 and inclined rings 44. Both sets of rings 42, 44 are preferably aligned along a common longitudinal axis 46. The combination of rings 42, 44 are joined by interconnecting links 48. In this embodiment, the inclined rings 44 are at one section while the upright rings 42 are at another section. Of course, it is contemplated that the inclined rings 44 may be at both ends with the upright rings 42 situated in the center, or the upright rings 42 are positioned at both ends with the inclined rings 44 at the center. In various alternative embodiments, it is possible to intersperse sections of inclined rings along other sections of upright rings, or any combination thereof. The spacing between rings does not need to be even as shown in FIG. 7.

As seen in the exemplary embodiments of FIGS. 6 and 7, each inclined planar ring 32, 44 is fully contained circumferentially within a theoretical plane. The inclined rings 44 are preferably tilted at a constant angle so that those planes are parallel to each other. It is contemplated that, in an alternative embodiment, the angle of tilt can vary within a single stent so the resulting planes are not necessarily parallel to each other. The angle or degree of tilt or inclination of the rings is ideally set structurally by the interconnecting links 34, 48, or by whatever structure is used to interconnect the inclined rings together.

The exemplary embodiments of the inclined planar ring stent are distinguishable from a corkscrew or helical winding rings found in stents having a coiled spring configuration, such as that shown in U.S. Pat. No. 4,886,062 (Wiktor) for example. Each coil or turn of such a coiled spring stent cannot be contained circumferentially within a plane since the coil has a helical form that extends out of the plane.

Moreover, by the predetermined arrangement of the parallel circumferential planes containing the rings of the present invention stent, it is possible to more precisely control the orientation and positioning of the deployed rings relative to a lesion, and the interconnecting links can be located to minimize bunching of the deployed rings, as seen in a coiled spring stent. Around bends in an artery, for example, the inclined ring stent has interconnecting elements that precisely orient and position each ring, while a coiled spring configuration stent with unsupported coils when deployed might have randomly spaced coils, have coils that topple or tilt too far offering too little arterial support, or have coils that tilt too little possibly injuring the vulnerable plaque because of the unintended high hoop strength.

FIGS. 8(a) and 8(b) illustrate one embodiment of an inclined ring stent in the compressed or crimped state, FIG. 8(a), versus the expanded or deployed state, FIG. 8(b). In the compressed state, the stent 50 has inclined rings 52 that "lie down," increasing the $\alpha$ or $\beta$ angle. As seen in FIG. 8(b), when the stent 50 is deployed, the inclined rings 52 "stand up" and decrease the $\alpha$ or $\beta$ angles. The dashed lines at the opposite ends of the diagrams of the stents are merely to show that the stent 50 still maintains a generally tubular shape.

FIGS. 10(a) and 10(b) illustrate another advantage of the present invention inclined ring or strut pattern. FIG. 10(a) shows a conventional upright ring of a prior art stent deployed within a vessel or body lumen 56. The radially outward expansion force of the ring 54 directly creates a reactive force in the vessel wall 56, indicated by the arrows. On the other hand, in FIG. 10(b), an inclined ring 58 of the identical dimensions, hoop strength, material construction, etc. as that shown in 54 but is inclined at an angle $\alpha$ thereby decreasing the radial component pressing against the vessel wall 56. In other words, the inclined ring 58 while maintaining vessel support at a lesion also is gentler on the lesion than a conventional upright ring 54.

This advantage is further illustrated in a simplified diagram of another embodiment of the present invention stent 60 shown in FIG. 9. In this side elevational view, the stent 60 is deployed adjacent the vulnerable plaque 27. The inclined rings 62 have a gentle bend generally at the intersection of the interconnecting links 64 with the rings 62. Based on the principle depicted in FIGS. 10(a) and 10(b), the inclined rings 62 due to their angular engagement of the vessel wall and the vulnerable plaque, the radial component of the outward radial force is diminished so that pressure on the vulnerable plaque 27 is lowered. The gentle pressure of the inclined rings and struts of the stent 60 thus minimizes or diminishes the possibility of inadvertently rupturing the vulnerable plaque 27.

Also depicted in FIG. 9 is another optional feature of the present invention. Specifically, from a side elevational view, the deployed ring can bend at any point along its circumference so when seen in a profile view, the ring bends at the 4 and 8 o'clock positions shown in FIG. 9, and bends at the 2 and 10 o'clock positions shown in FIG. 3. These chord bends 61 as they appear in the profile view are not possible in a coiled spring stent since each individual coil is unsupported at the bend point by interconnecting links. Consequently, as seen in FIG. 3 or 9, the chord bend 61 allows the inclined rings to engage the vulnerable plaque at the 12 o'clock position in one angular attitude, and engage the healthy intraluminal wall at the 6 o'clock position in another angular attitude.

Figure 12:
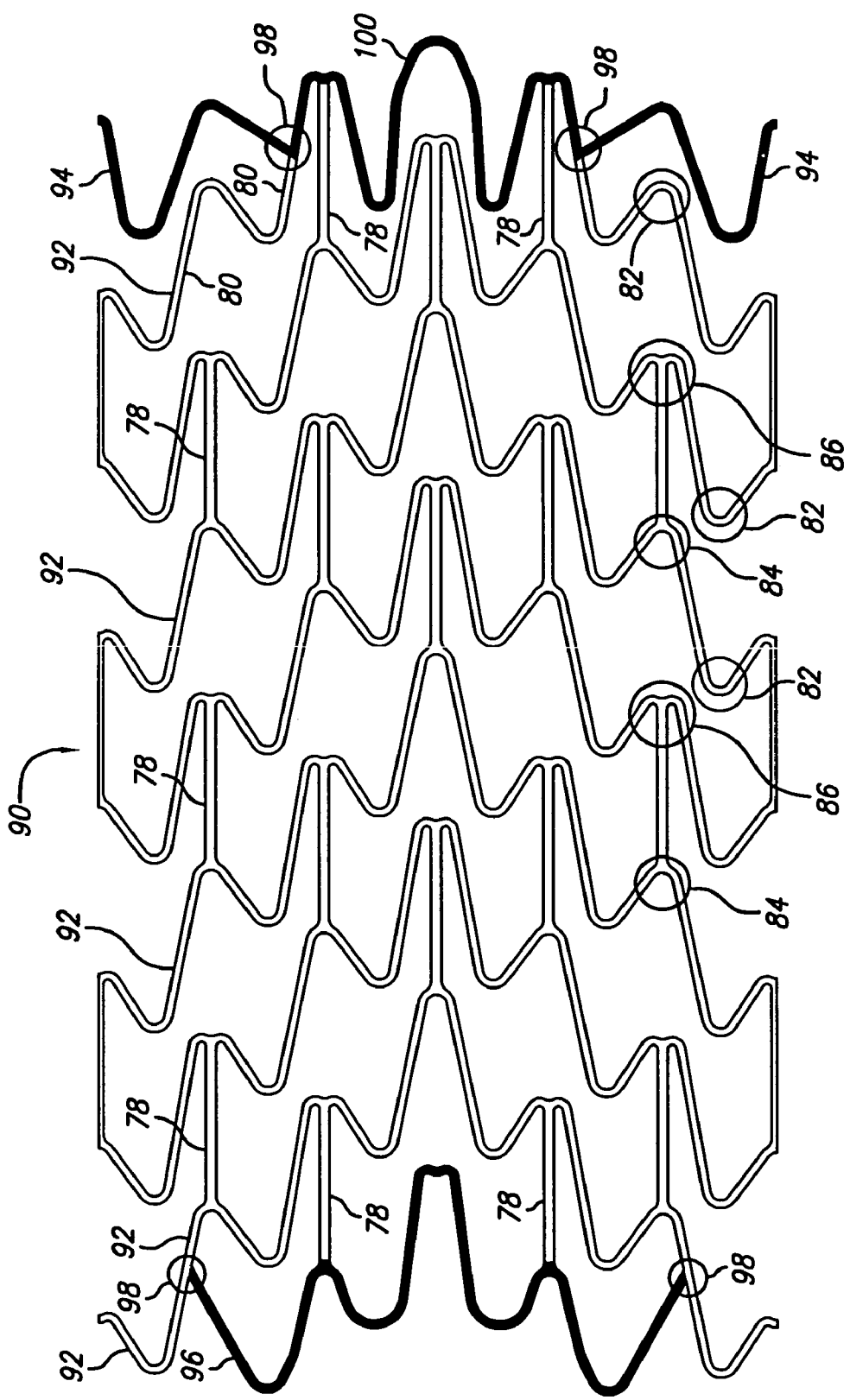
FIG. 12 is another embodiment of the present invention stent unrolled and flattened to show the inclined ring strut pattern with upright rings at the ends.
Figure 13:
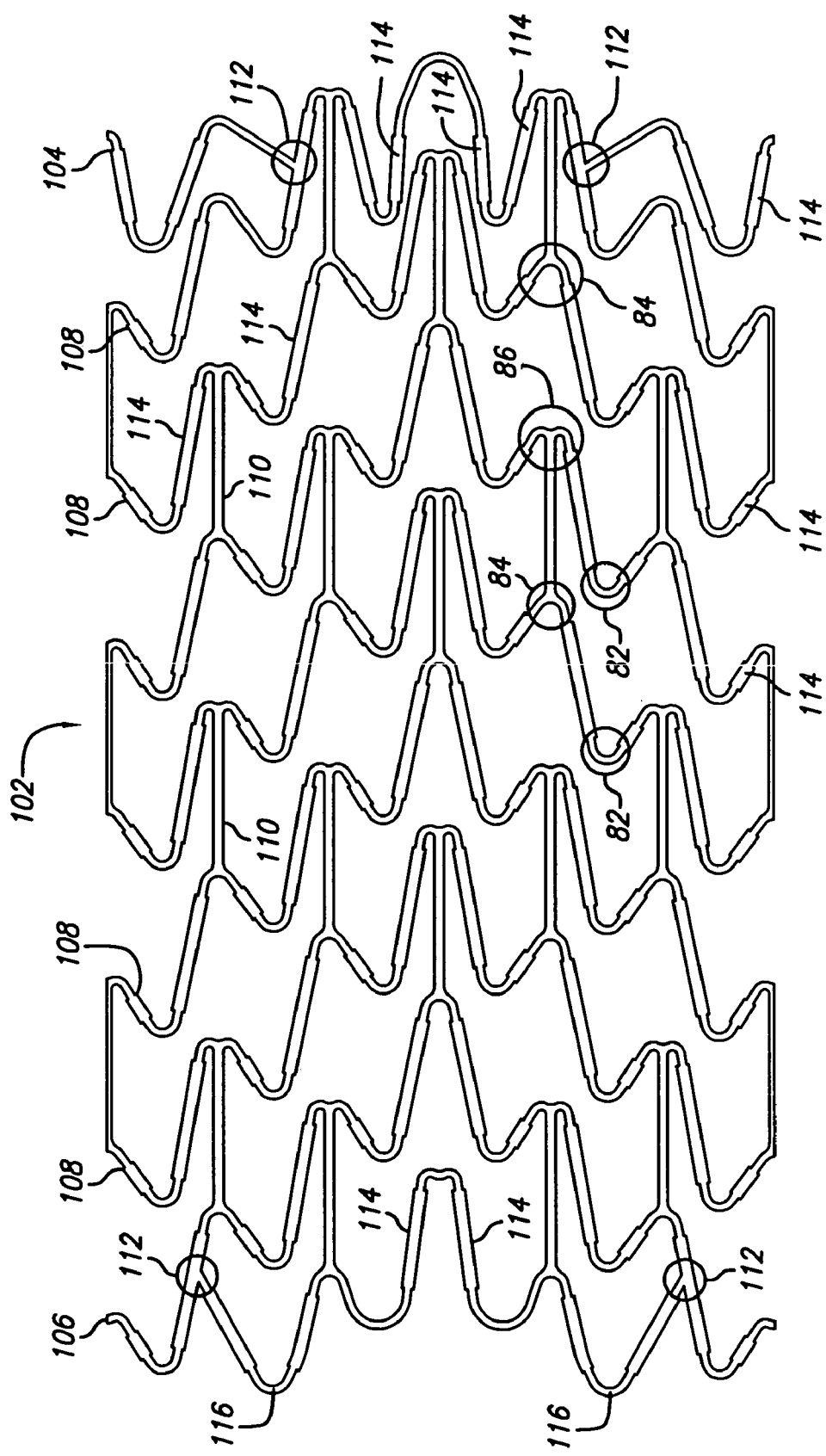
FIG. 13 yet another embodiment of the present invention stent unrolled and flattened to show the inclined ring strut pattern with enlarged struts.

FIGS. 11–13 are plan views of various embodiments of the present invention inclined ring stent that have been unrolled and flattened into two dimensions for illustration of the strut pattern.

In the exemplary embodiment shown in FIG. 11, the stent 70 has a distal end 72 and a proximal end 74. One inclined ring 76 near the distal end 72 has been completely shaded in black to highlight its structure. In this unrolled, flattened sheet depiction, the ring 76 appears to assume a V-shape configuration. When the sheet is rolled into a tube and viewed from a profile, however, the rings 76 then appear inclined relative to a vertical axis as explained earlier. The inclined rings 76 are arranged adjacent one another with a common longitudinal axis that extends the length of the stent 70. Adjacent rings 76 are joined to each other by interconnecting links 78 or the like. In this embodiment, the interconnecting links 78 are preferably straight and/or aligned with the common longitudinal axis. They are further optionally aligned axially in a column with a link missing between every other ring 76.

Each ring 76 is generally made from a serpentine wave pattern of interconnected straight sections called arms or struts 80 joined by vertices or crests more precisely called peaks and valleys 82, 84. The arms or struts 80 extending from a common vertex 82, 84 may be of equal length or unequal length. Essentially, the strut pattern is a first column of vertices, and a second column of vertices spaced 180° circumferentially apart from the first column where both columns of vertices have two arms of equal lengths, and the remaining vertices have arms of unequal lengths.

Using different nomenclature than peaks and valleys, each ring 76 can be characterized as having U-, W-, and Y-shaped portions. In FIG. 11, a U-shaped portion has been designated with reference number 82. A Y-shaped portion has been designated with reference number 84. A W-shaped portion has been designated with reference number 86. Therefore, to describe the strut pattern of the embodiment shown in FIG. 11 using these identifiers, each ring 76 is composed of six U-shaped portions 82, three Y-shaped portions 84, and three W-shaped portions 86. Adjacent rings 76 are joined by interconnecting links 78 wherein the interconnecting link 78 extends from a Y-shaped portion 84 to a W-shaped portion 86 of the adjacent ring.

In the embodiment shown in FIG. 11, the interconnecting links 78 are preferably used to join a peak 66 of one ring to the peak 66 of an adjacent ring. In various alternative embodiments, it is contemplated to join, by use of a interconnecting link, the valley of one ring to the valley of an adjacent ring, or to connect via interconnecting link the valley of one ring to the peak of an adjacent ring, or any combination of the foregoing.

Still in FIG. 11, the embodiment contains interconnecting links 78 that form generally an end-to-end columns, parallel to the stent axis, that are spaced apart circumferentially by about 120 degrees. The interconnecting links are, as mentioned above, preferably aligned lengthwise along an axis parallel to the longitudinal axis of the stent with a gap or missing link between every other ring 76. More or fewer interconnecting links 78 are contemplated and their circumferential spacing can be changed to suit various strength or vessel support requirements.

FIG. 12 shows an alternative embodiment stent 90 again with inclined rings 92, but wherein the end rings 94 are upright as generally shown in FIG. 7. The upright end rings 92, 94 are joined to each other by straight interconnecting links 78. To better illustrate the upright end rings 94, 96, they have been completely darkened in black ink. Conceptually speaking, as seen in FIG. 12, the upright end rings 94, 96 are appended to the inclined rings 92 mostly by the interconnecting links 78 except at joints 98. The joint 98 is a bifurcation, intersection, or confluence where the upright end ring 94, 96 meets a strut 80 of an inclined ring 92. The joint 98 may be a real joint that is a bond, weld, braze, or fusion of two components, or if the stent is cut or fashioned from a single sheet or piece of material, the joint 98 and its component parts are entirely integral with each other.

The exemplary strut pattern shown in FIG. 12 further has an optional bulbous peak 100. The bulbous peak 100 is useful for improved vessel or tissue support at the end of the stent 90. The remainder of the strut pattern contains U-shaped portions 82, Y-shaped portions 84, and W-shaped portions 86.

Conceptually speaking, another feature of the FIG. 12 embodiment is that the inclined ring 92 adjacent the distal upright ring 94 is incomplete since the strut terminates at joint 98. Of course, this is only a theoretical convention for understanding the strut pattern and the strut itself may or may not actually terminate at that location based on fabrication techniques as explained above relative to joint 98.

The stent in FIG. 12 has upright end rings 94, 96 to improve support for the vessel based on greater hoop strength at the opposite ends of the stent 90. Typically, the hoop strength of the end rings are not as strong as the rings in the middle section since the end rings are supported only on one side. Therefore, the upright end rings 94, 96 provide extra hoop strength and vessel support at those locations so that the radial strength along the entire length of the stent 90 is relatively consistent.

FIG. 13 is an alternative embodiment stent 102 having a strut pattern nearly identical to that shown in FIG. 12. The stent 102 contains upright end rings 104, 106 at the distal and proximal ends, respectively, with inclined rings 108 along the middle portion of the stent. The upright and inclined rings 106 are joined to each other as explained above relative to FIG. 12 with interconnecting links 110 and at joints 112.

The most apparent difference is that the arms or straight strut sections 114 have increased mass or girth relative to other areas of the stent, most apparently at the interconnecting links 110 and the vertices, i.e., the U-shaped portions 82, Y-shaped portions 84, and W-shaped portions 86. The increased mass straight strut section 114 is useful to improve radiopacity of the stent 102 when viewed under x-ray or a fluoroscope. This helps the physician visualize and locate the stent at the deployment site. The increased mass arms or straight sections 114 do not increase bulk at the vertices, i.e., the U-, Y-, and W-shaped portions 82, 84, 86 so that the ease of deployment based on expansion pressure of the expandable member or balloon does not need to be increased.

In the alternative, of course, it is possible to begin with a stent such as that shown in FIG. 12 and pare down the mass at the U-, Y-, and W-shaped portions 82, 84, 86 instead of increasing the mass at the straight strut sections 114. The mass may be removed by decreasing the width, thickness, or curvature, or creating a groove or cut-out 116 in the vertex or crest at the U-, Y-, and W-shaped portions 82, 84, 86. With a cut-out or groove, material is removed from the center of the vertex or crest so the force needed to deploy the stent is lowered yet the overall thickness of the strut is not. Also, a significant reduction in the deployment pressure for the balloon catheter can be achieved by narrowing the vertex or crest by around about 25%–30% and more preferably about 30%. The percent narrowing can be a function of mass reduction or cross-sectional area reduction. In the embodiment shown in FIG. 12, with the narrowed vertices or crests, the preferred strut width/strut thickness ratio is preferably 1 or higher. Naturally, all of the alternative embodiments described above with their modifications are also contemplated here with respect to the embodiments shown in FIGS. 12 and 13.

In still other alternative embodiments, any portion of the disclosed stents can be made from a metal alloy or from a polymer. For example, the rings can be made from a metal alloy while the connecting links can be made from a metal alloy or a polymer. Typically, if the links are made from a polymer, the stent will be more longitudinally flexible than if the links were made from a metal alloy. Also, the anchors can be made from either a metal alloy or a polymer.

Exemplary of the metallic material used in forming the rings, links, and/or struts of the stent are stainless steel, titanium, nickel-titanium, tantalum, gold, cobalt-chromium, platinum, palladium, iridium, or any combination or alloys thereof. As for nickel-titanium, specifically superelastic nickel-titanium alloys that benefit from reversible, isothermal phase transformations from austenite to stress-induced martensite and back are contemplated. Such a nickel-titanium alloy stent would be self-expanding and would not require a balloon dilatation catheter for deployment. Other metals, metal alloys and polymers may also be used to form the present invention stent.

The rings and links are optionally configured so that the metallic surface area (metal-to-artery ratio) is preferably less than about 20%, and more preferably is between about 20% and 10%, thus providing good scaffolding and providing a more cylindrical lumen.

Exemplary of the biocompatible polymer material used in forming the rings, the links or the anchors includes the group of polymers consisting of polyurethanes, polyetherurethanes, polyesterurethanes, silicone, thermoplastic elastomer (C-flex), polyether-amide thermoplastic elastomer (Pebax), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton) and polyester thermoplastic elastomer (Hytrel), polyethylene, polylactic acid (PLA), polyglycolic acid (PGA), and polylactic-co-glycolic acid (PLGA).

The present invention stent may also be used in connection with a drug or therapeutic agent to perform a variety of functions, from preventing blood clots to promoting healing. Further, it is well known that the stent (when made from a metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent.

As an example, an active agent coating on the rings, links and/or struts can inhibit the activity of endothelial cells. Similarly, an active agent coating on selective rings, links and/or struts can also inhibit the activity of smooth muscle cells. More specifically, the active agent is aimed at inhibiting abnormal or inappropriate migration and proliferation of smooth muscle cells. The active agent can also include any substance capable of exerting a therapeutic or prophylactic effect in the practice of the present invention. The agent can also be for enhancing wound healing in a vascular site or improving the structural and elastic properties of the vascular site. The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, anti-inflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, Adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as platelet-derived growth factor (PDGF) receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. Furthermore, the calculation of dosages, dosage rates and appropriate duration of treatment are previously known in the art.

Representative examples of polymers that can be used to coat a stent in accordance with the present invention include ethylene vinyl alcohol copolymer (commonly known by the generic name EVOH or by the trade name EVAL), poly (hydroxyvalerate); poly(L-lactic acid); polycaprolactone; poly(lactide-co-glycolide); poly(hydroxybutyrate); poly(glycolic acid); poly(hydroxybutyrate-co-valerate); polydioxanone; polyorthoester; polyanhydride; poly(D,L-lactic acid); poly(glycolicacid-co-trimethylene carbonate); polyphosphoester; polyphosphoester urethane; poly(amino acids); cyanoacrylates; poly(trimethylene carbonate); poly (iminocarbonate); copoly(ether-esters) (e.g. PEO/PLA);

polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; polybutylmethacrylate; rayon; rayon-triacetate; poly(glycerol-sebacate); cellulose acetate; cellulose butyrate; cellulose acetate butyrate; cellophane; cellulose nitrate; cellulose propionate; cellulose ethers; and carboxymethyl cellulose.

"Solvent" is a liquid substance or composition that is compatible with the polymer and is capable of dissolving the polymer at the concentration desired in the composition. Representative examples of solvents include chloroform, acetone, water (buffered saline), dimethylsulfoxide (DMSO), propylene glycol methyl ether (PM,) iso-propylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, pentane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof. Therapeutic substance contained in the coating can be for inhibiting the activity of vascular smooth muscle cells. More specifically, therapeutic substance can be aimed at inhibiting abnormal or inappropriate migration and/or proliferation of smooth muscle cells for the inhibition of restenosis. Therapeutic substance can also include any active agent capable of exerting a therapeutic or prophylactic effect in the practice of the present invention. For example, therapeutic substance can be for enhancing wound healing in a vascular site or improving the structural and elastic properties of the vascular site.

The stent of the present invention can be made in many ways. One method of making the stent is to cut a thin-walled tube, from stainless steel tubing for example, to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cutting the stent pattern, the stent is preferably electrochemically polished in an acidic aqueous solution such as a solution of ELECTRO-GLO #300, sold by ELECTRO-GLO Co., Inc. in Chicago, Ill., which is a mixture of sulfuric acid, carboxylic acids, phosphates, corrosion inhibitors and a biodegradable surface active agent. Other electropolishing solutions are well known in the art. The stent may be further treated if desired, for example by applying a biocompatible coating such as described above.

Other methods of forming the stent of the present invention can be used, such as chemical etching; electric discharge machining; laser cutting a flat sheet and rolling it into a cylinder, and the like, all of which are well known in the art at this time.

While the invention has been illustrated and described herein in terms of its use as an intravascular stent, it will be apparent to those skilled in the art that the stent can be used in other body lumens. Other modifications and improvements may be made without departing from the scope of the invention.

What is claimed is:

1. An intraluminal stent, comprising:
a plurality of planar rings aligned along a common longitudinal axis and contained within a first end section, a middle section, and a second end section;
wherein each ring is defined by a circumference entirely contained within a plane;
wherein only the first end section includes at least one ring having the inclined circumferential plane and the remaining circumferential planes are perpendicular to the common longitudinal axis; and
a plurality interconnecting members having a length extending parallel to the common longitudinal axis and joining adjacent rings.

2. The intraluminal stent of claim 1, wherein the inclined circumferential planes are parallel to each other.

3. The intraluminal stent of claim 1, wherein the inclined circumferential planes are tilted at an angle $\alpha$ defined by about $30° \leq \alpha \leq$ about $45°$ when the stent is deployed in a body lumen.

4. The intraluminal stent of claim 1, wherein the interconnecting members are straight and form at least two columns disposed circumferentially apart.

5. The intraluminal stent of claim 1, wherein each ring includes a serpentine strut pattern having alternating vertices and arms, and wherein at least some of the vertices include a reduced cross-sectional area relative to the arms.

6. The intraluminal stent of claim 1, wherein each ring includes a serpentine strut pattern having alternating vertices and arms, and wherein at least some of the vertices include a reduced mass section.

7. The intraluminal stent of claim 1, wherein each ring includes a serpentine strut pattern having alternating vertices and arms, and wherein at least some of the vertices include a void for reduced strength.

8. The intraluminal stent of claim 1, wherein each ring includes a serpentine strut pattern having alternating vertices and arms, and wherein at least some of the vertices include a groove for reduced strength.

9. The intraluminal stent of claim 1, wherein each ring includes a serpentine strut pattern having alternating vertices and arms, and wherein at least some of the vertices are radially thinner than the arms.

10. The intraluminal stent of claim 1, wherein each ring includes a serpentine strut pattern having alternating vertices and arms, and wherein at least some of the vertices are narrower circumferentially for reduced strength.

11. An intraluminal stent, comprising:
a plurality of rings aligned along a common longitudinal axis;
wherein some of the rings are contained circumferentially by respective circumferential planes, and the circumferential planes are inclined relative to a plane perpendicular to the longitudinal axis;

interconnecting members joining adjacent rings, wherein the interconnecting members and the rings lie in a common tangential plane; and wherein some of the inclined rings include a chord bend at a circumference when deployed inside a body lumen.

12. The intraluminal stent of claim 11, further comprising rings having a first column of vertices and a second column of vertices spaced 180° circumferentially apart from the first column have two arms of equal lengths and the remaining vertices have arms of unequal lengths.

13. The intraluminal stent of claim 12, wherein a plurality of the arms include a greater cross-sectional area at a middle section of the arm relative to the ends thereof.

14. The intraluminal stent of claim 11, wherein the stent includes an end ring at opposite ends thereof, and each end ring is defined circumferentially by a plane that is perpendicular to the common longitudinal axis.

15. The intraluminal stent of claim 11, wherein the interconnecting members are aligned longitudinally parallel to the common longitudinal axis and spaced with gaps between adjacent rings.

16. An intraluminal stent, comprising:

a plurality of rings aligned along a common longitudinal axis and contained with respective planes, wherein some of the rings are inclined relative to a plane perpendicular to the common longitudinal axis;

each ring having a serpentine strut pattern including at least two arms terminating at a common vertex, wherein at some vertices the two arms have unequal lengths and at other vertices the two arms have equal lengths;

a plurality of straight interconnecting members disposed parallel with the common longitudinal axis joining adjacent rings; and wherein the inclined rings include a chord bend at a circumference thereof when deployed inside a body lumen.

17. The intraluminal stent of claim 16, wherein the planes containing the inclined rings are parallel to each other.

18. An intraluminal stent, comprising:

a plurality of planar rings aligned along a common longitudinal axis and contained within a first end section, a middle section, and a second end section;

wherein each ring is defined by a circumference entirely contained within a plane;

wherein only the first and the second end sections include at least one ring having the inclined circumferential plane and the remaining circumferential planes perpendicular the common longitudinal axis; and a plurality interconnecting members having a length extending parallel to the common longitudinal axis and joining adjacent rings.

19. An intraluminal stent, comprising:

a plurality of planar rings aligned along a common longitudinal axis and contained within a first end section, a middle section, and a second end section;

wherein each ring is defined by a circumference entirely contained within a plane;

wherein only the first end section and the middle section include at least one ring having the inclined circumferential plane and the remaining circumferential planes are perpendicular to the common longitudinal axis; and a plurality interconnecting members having a length extending parallel to the common longitudinal axis and joining adjacent rings.

20. An intraluminal stent, comprising:

a plurality of planar rings aligned along a common longitudinal axis and contained within a first end section, a middle section, and a second end section;

wherein each ring is defined by a circumference entirely contained within a plane;

wherein only the middle section includes at least one ring having the inclined circumferential plane and the remaining circumferential planes perpendicular to the common longitudinal axis; and a plurality interconnecting members having a length extending parallel to the common longitudinal axis and joining adjacent rings.

* * * * *